United States Patent [19]
Mansuria et al.

[11] Patent Number: 4,696,578
[45] Date of Patent: Sep. 29, 1987

[54] SINGLE CHIP THERMAL TESTER

[75] Inventors: Mohanlal S. Mansuria, Coral Springs, Fla.; Rolf G. Meinert, Wappingers Falls, N.Y.; Sevgin Oktay, Poughkeepsie, N.Y.; Carl D. Ostergren, Montgomery, N.Y.

[73] Assignee: International Business Machines Corporation, Armonk, N.Y.

[21] Appl. No.: 876,143

[22] Filed: Jun. 19, 1986

[51] Int. Cl.4 .................. G01N 25/00; G01R 31/26
[52] U.S. Cl. ................................. 374/45; 324/158 R
[58] Field of Search .................. 374/29, 45, 43, 44; 324/158 T, 158 F; 364/557

[56] References Cited
U.S. PATENT DOCUMENTS

| | | | |
|---|---|---|---|
| 3,720,103 | 3/1973 | Adams et al. | 374/29 |
| 3,745,360 | 7/1973 | Belzer et al. | 324/158 T |
| 3,842,346 | 10/1974 | Bobbitt | 324/158 F X |
| 3,906,363 | 9/1975 | Fowler | 324/158 F |
| 4,123,938 | 11/1978 | Hamilton | 374/29 |
| 4,396,300 | 8/1983 | Characklis et al. | 374/43 |
| 4,522,512 | 6/1985 | Atkins | 374/44 X |
| 4,604,572 | 8/1986 | Horiuchi | 324/158 R X |

Primary Examiner—Daniel M. Yasich
Attorney, Agent, or Firm—John D. Crane

[57] ABSTRACT

A thermal tester for measuring the efficiency of a heat transfer device for cooling semiconductor chips is disclosed having a positioning means operable to position the heat transfer device in thermal contact with the chip. The positioning means is adjustable in at least 5 degrees of freedom. Temperature sensors are provided to sense the temperature of the chip, the chip support substrate and the positioning means adjacent the heat transfer device. Means is provided to dispose the chip and heat transfer device in a vacuum. Control means is also provided to adjust the temperature of the chip unitl it is the same as the substrate to thereby assure heat transfer occurs only from the chip to the positioning means by way of the heat transfer device. When this thermal balance is achieved the thermal resistance of the heat transfer device can be calculated.

24 Claims, 7 Drawing Figures

SINGLE CHIP THERMAL TESTER

FIELD OF THE INVENTION

The present invention relates broadly to the field of semiconductor manufacture and use and particularly to an apparatus for precisely measuring the thermal characteristics of heat transfer devices used with semiconductor chips to keep the operating temperature thereof from becoming too high.

BACKGROUND OF THE INVENTION

As the ability of semiconductor manufacturers to reduce the physical size of circuits has improved, the power dissipation in the circuits so manufactured has accordingly increased. As a result, it has become increasingly necessary to provide some form of cooling for integrated circuit chips and modules. In relatively low circuit density applications, forced air with suitable space air conditioning has proved to be sufficient. However, as circuit density increases, the heat dissipation requirements increase as well. In such environments, more effective cooling techniques than using forced air are required. The higher efficiency cooling techniques that have been used frequently include the use of water cooling and the like. Various cooling devices are also required to transfer the heat form its source on a chip to a water cooling jacket.

While it is well understood that in situations involving high circuit density that effective cooling is required in order to maintain chip operating temperatures at acceptable levels, the techniques available for measuring the thermal performance of various cooling approaches has not proved to be as accurate as is desired. As a consequence, design of suitable cooling systems typically have required a great deal of over capacity in order to assure that the desired operating chip temperature is not exceeded.

Various approaches are known in the prior art for measuring heat flow. One such approach is illustrated in U.S. Pat. No. 3,720,103 which relates to a heat flux meter. In that device, thermocouples are used to measure the temperature differential between two surfaces. The sensed temperature difference controls a heater which is adjusted so that heat flow between the surfaces is prevented. The first surface is shielded from the environment to prevent heat flow therefrom to this surface. This device, however, is not suitable for measuring the performance of a cooling device such as a heat sink or heat transfer device used in a semiconductor module for cooling a semiconductor chip or the like.

A method and apparatus for determining the thermal resistance in semiconductors is illustrated in U.S. Pat. No. 3,745,460. In this approach, a current pulse is fed into the semiconductor causing heat to be generated therein. The detected time interval between cessation of the pulse and detection of maximum heat transfer leads to a determination of the thermal resistance.

A method and apparatus for determining the heat transfer characteristics of a tube is described in U.S. Pat. No. 4,396,300. The apparatus includes an electric heater for heating a block which surrounds and engages part of the tube. A liquid is pumped through the tube and a thermistor is used to measure the fluid temperature. A pressure drop sensor is provided to sense the drop in pressure across the block. The sensed data is transferred to a computer for computing the heat transfer resistance. Like the other approaches mentioned above, this method too is not suitable for determining the effectiveness of a heat transfer device used in a module to cool a semiconductor chip.

BRIEF DESCRIPTION OF THE INVENTION

In view of the problems associated with the above mentioned prior art apparatus, it is the primary object of the present invention to provide a highly accurate device for measuring the thermal resistance of a heat transmitting device, such as a heat sink or the like.

It is another object of the invention to provide a device for precisely measuring the thermal resistance of a cooling device used in a semiconductor module for cooling a chip housed therein.

It is yet another object of the invention to provide a thermal resistance measuring device for precisely measuring the thermal resistance of a cooling device for cooling a semiconductor chip for which measuring device is easily adjusted to accommodate different cooling device designs and configurations.

It is yet another object of the invention to provide a thermal resistance measuring device for precisely measuring the thermal resistance of the interfaces disposed between the chip and the body which cools the chip, the interfaces and the cooling device.

In accomplishing these and other objects of the invention, the present invention is directed to a device for measuring the thermal characteristics of a cooling device or a heat transfer device such as a heat sink for use with a semiconductor chip and particularly to measuring the thermal resistance thereof. The tester of the present invention includes a base to which a heat source is bonded in a thermal transmitting manner. The heat source is made in the size and configuration of a chip which is to be cooled by a cooling device which is to be tested. A positioner for the cooling device is provided for locating the cooling device at precisely the desired position in intimate thermal contact relationship with the heat source. Temperature sensors are provided on the heat source, on the substrate carrying the heat source and on the positioner or the cooling device. Means cooperative with the base and the positioner are provided to adjust the temperature of the base and the positioner. The substrate temperature is adjusted until it is the same as the desired operating temperature for the chip. The temperature of the positioner or the cooling device is then set. Thereafter, power is applied to the heat source and adjusted until the chip temperature becomes the same as that of the substrate. When the system is in thermal balance in the steady state as indicated by the fact that the chip and substrate temperatures are the same, the thermal resistance of the heat flow path from the heat source to the positioner can be determined from the equation $(T_C - T_D)/CP$ where $T_C$ is the chip temperature, $T_D$ is the temperature of the coolant and CP is the power in watts to the chip. To prevent heat convection from the heat source and heat sink from adversely affecting the measurement, the apparatus of the present invention is disposed in a vacuum chamber. In the event a different atmosphere is desired, the vacuum chamber can be first evacuated and the desired atmosphere gas introduced into the chamber thereafter.

The apparatus of the present invention is very useful in measuring thermal resistance because it is sensitive to the efficiency of the cooling device and to increased power to the chip. This makes it possible to use the invention in applications where chip power can be an order of magnitude greater than is achievable with other testers now known.

BRIEF DESCRIPTION OF THE DRAWINGS

The foregoing and other objects, advantages and features of the present invention are described below in greater detail in connection with the drawings which form a part of the disclosure wherein.

DETAILED DESCRIPTION

Figure 1:
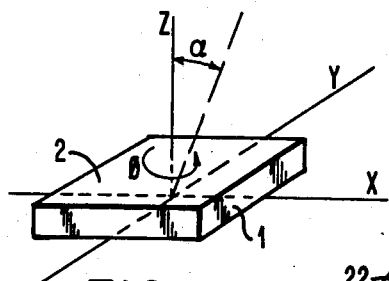
FIG. 1 is a sketch illustrating the types of adjustment which must be achieved by the apparatus of the present invention in order to permit the cooling device to be tested in positions which approximate those which would occur in manufactured products.

Referring first to FIG. 1, the three dimensional solid body 1 is illustrative of a typical VLSI semiconductor chip although other configurations for such chips may be utilized. For reasons of clarity with respect to describing FIG. 1, the connector pins and the substrate on which the semiconductor chip is mounted are not shown. In FIG. 1, the body 1 has a shape which is typical for a semiconductor chip and is square as illustrated, although it could be rectangular, in all planes passing therethrough and disposed parallel to the x-y plane. The body 1 is rectangular in shape in all planes passing therethrough and disposed parallel to the x-z plane. The height of the body 1 in the z direction is small compared to the dimension in the x or the y direction.

If heat is produced in the chip 1 and is to be conducted away from the upper surface 2, a cooling means or heat transfer device such as a heat sink or the like, not shown, should be positioned to contact the surface 2. The heat transfer device would preferably be in thermal contact with the upper surface of the body 2 and have a lower surface designed for contacting the upper surface 2 in a specified manner so as to provide a desired cooling thereof by allowing heat to flow therefrom. The term thermal contact as used in this patent implies that two bodies are touching each other thereby providing a direct thermal transfer path therebetween. The thermal transfer path between two contacting bodies may be enhanced by the use of a thermal paste, a heat conductive gas, a metallurgical bond or other thermal interface material between the two bodies to fill the tiny imperfections in the mating surfaces so as to provide a low thermal resistance for the thermal path between the two bodies.

If one could assume that the upper surface 2 is truly a plane which is parallel to the x-y plane and the heat transfer device designed to contact it is movable in the z direction and lies in a plane parallel to the x-y plane, then the heat transfer device would need only be movable in the z direction to come into thermal contact with the surface 2. To further assure alignment of the surface 2 with the heat sink surface designed to contact the surface 2, it may be necessary to be able to rotate the body 1 in the x-y plane about the z axis as illustrated by the rotational angle $\Phi$.

In actual situations of testing a semiconductor chip, the chip is mounted on a substrate surface such as the x-y plane of FIG. 1 and the upper surface 2 of the chip 1 may not precisely lie in a plane parallel to the x-y plane. In such a situation, in order for the heat transfer device to properly contact the surface 2, the orientation of the surface of the heat transfer device designed to contact the chip may have to be adjusted by, for example, moving the z axis by an angle $\alpha$ which is the between the z axis when disposed orthogonal to the x-y plane and the location of the z axis in the x-z plane after it has been shifted to realign the direction of movement of the heat sink. Accordingly, in order to assure proper thermal contact between a heat transfer device and a semiconductor chip, the two must be movable relative to each other in the x, y, and z planes as well as rotating ($\Phi$) and tilting ($\alpha$). As such, the heat transfer device and the chip should be movable with respect to each other in at least 5 degrees of freedom in order to assure that the desired thermal contact can be established between them thereby assuring either the lowest thermal resistance of the contact between these two bodies or a thermal resistance which is what is desired for a particular situation.

If the semiconductor chip has a planar upper surface, it is possible to establish intimate thermal contact with a heat transfer device where the support mechanism for both establishes only 4 degrees of freedom of motion of the chip relative to the heat transfer device. This is accomplished by assuring that the planar contact surface of the chip is disposed in a plane normal to the direction of motion of the heat transfer device and also assuring that the mating surface of the heat transfer device lies in a plane parallel thereto.

Figure 2:
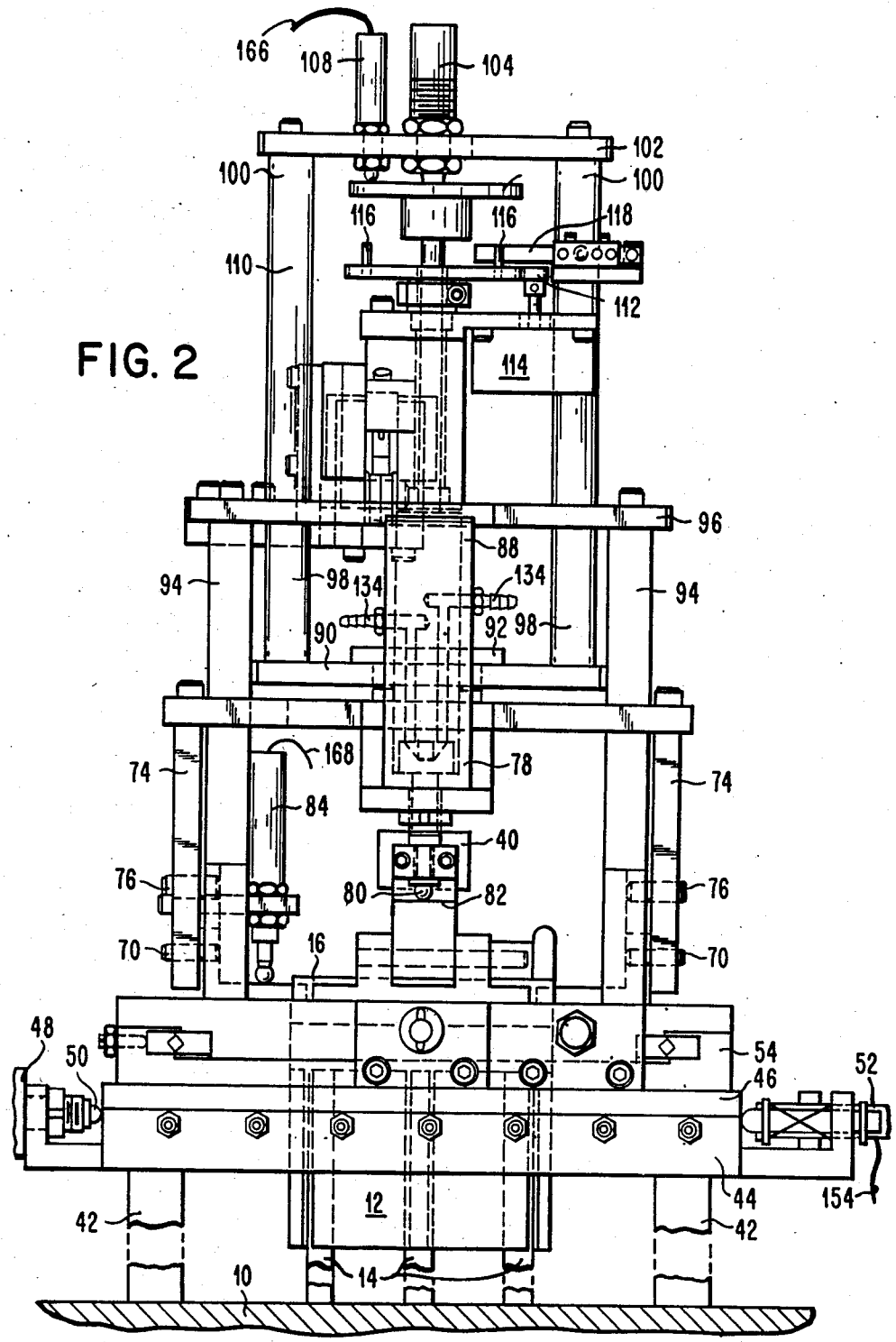
FIG. 2 is a front view of the apparatus for positioning the heat sink relative to the heat source.

Referring now to FIG. 2, the preferred embodiment of the present invention is illustrated and rests upon a base plane 10. A module support member 12 is supported on the base plane 10 by at least 3 support legs 14.

The module support member 12 has a module support ring 16 removably attached to the upper part thereof. The module support ring 16 is illustrated in greater detail in FIGS. 4 and 5. The module support ring has an essentially flat upper surface 18 with a plurality of holes 20 which pass therethrough and are designed for receiving a screw or the like thereby permitting the module support ring 16 to be secured to the remainder of the modules support number 12.

Located in the upper surface 18 of the module support ring 16 are three planar reference pins which project upwardly from the upper surface 18 a small distance thereby establishing a reference plane which is substantially parallel to the upper surface 18 and also comprises the plane in which the upper surface of the chip under test lies.

Disposed at the center of the upper surface 18 is a square opening 24 designed to receive a semiconductor module 26 or the like. The corners of the opening are drilled out as illustrated at 28 to permit a module 26 to be positioned in the opening 24 and have epoxy cement or the like forced into the holes 28 to thereby secure the module 26 to the module support ring 16. Normally, when a module 26 is positioned in the opening 24, a thermally conductive paste or the like is placed on the mating surfaces of the module 26 and the opening 24 so as to form a thermally conductive bridge between the module 26 and the module support ring 16.

Figure 4:
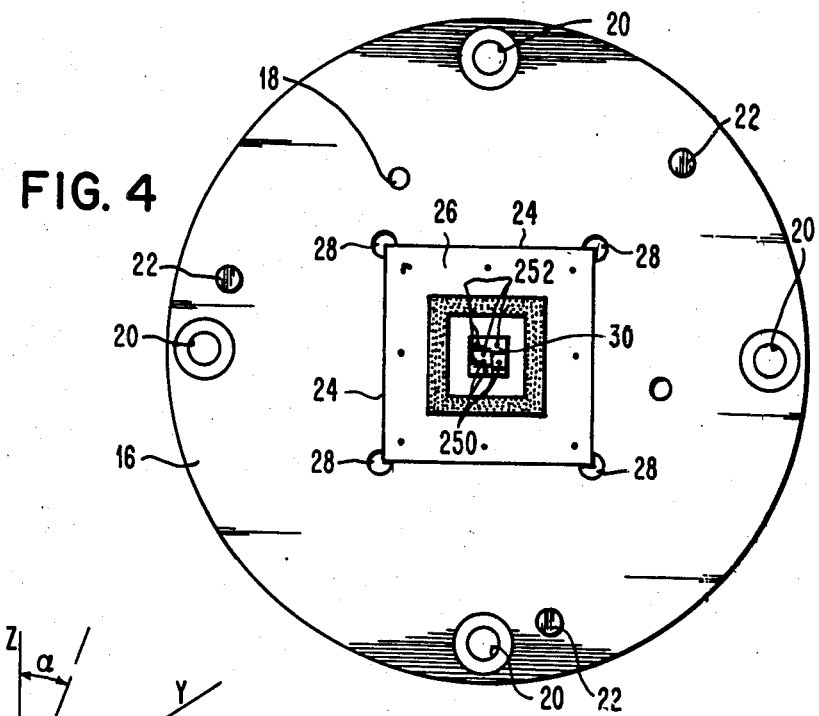
FIG. 4 is a perspective view of the upper surface of the module support member with a module disposed therein.
Figure 5:
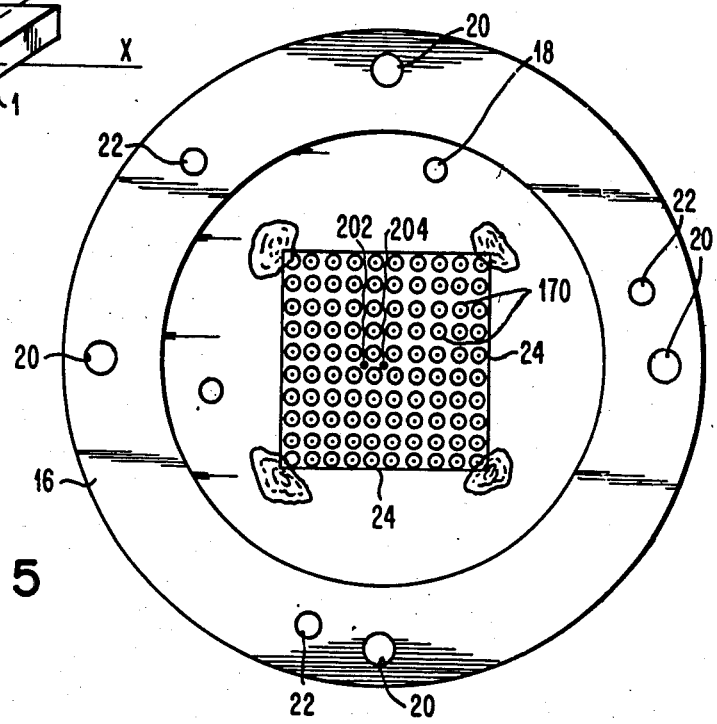
FIG. 5 is a perspective view of the lower side of the module support member showing a module disposed therein.
Figure 3:
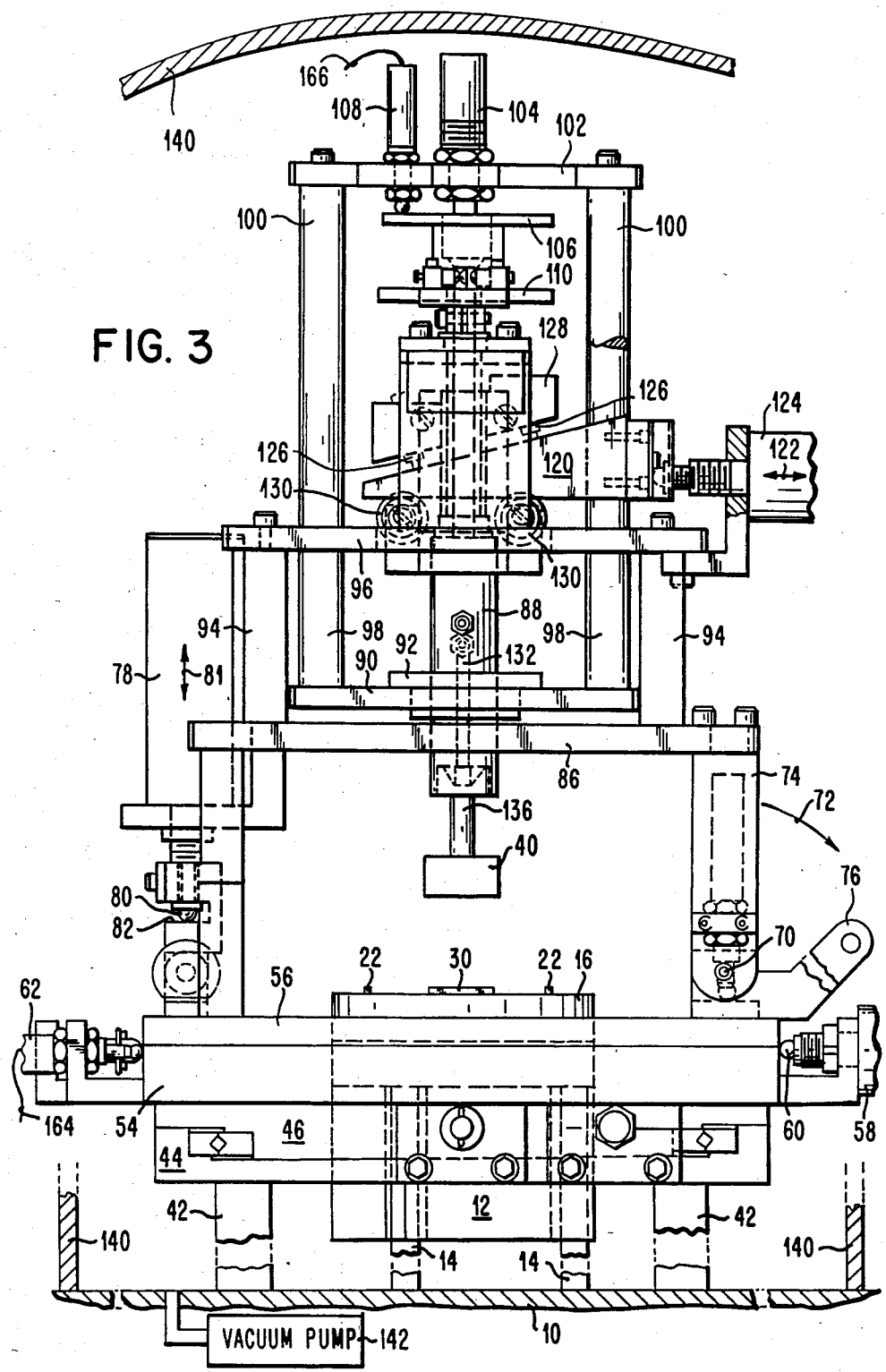
FIG. 3 is a side view of the apparatus illustrated in FIG. 2.

As viewed in FIG. 4, the module 26 has a chip 30 disposed at the center thereof. The chip 30 is mounted on the module 26 and projects upwardly from the upper surface thereof as is best illustrated in FIG. 3. As will become more apparent from the later discussion, it is important to assure that the upper surface of the chip 30 is disposed in a known plane. This is accomplished by resting the module support ring 16 on a planar support surface in a manner such that the upper surface 18 faces toward the planar surface on which the ring 16 rests. Then, a module is inserted into the opening 24 from the rear as illustrated in FIG. 5 and carefully pressed downwardly toward the planar support surface until the upper surface of the chip 30 rests firmly on the planar support surface. The module is then cemented into the opening 24 by placing a suitable cement into the corner holes 28 and allowing that cement to harden. Once the cement has hardened, the upper surface of the chip 30 will lie in the same plane as defined by the upper surface of the planar reference pins 22.

The module support member 12 and the ring 16 are preferably made out of a good thermal conducting metal material such as copper although silver could also be utilized. The module support member 12, as already mentioned, is supported above the base plane 10 by legs 14. These legs are preferably made of an insulating material thereby thermally isolating the module support member 12 from the material of the base 10. As it is important to be able to control the temperature of the module, the module support member 12 is largely hollow and is coupled by any suitable means to a liquid reservoir (not shown) and by means of pumping mechanism (also not shown) the liquid from the reservoir is circulated therethrough. The temperature of the liquid thereby causes the module support member 12 to become the same temperature as the liquid being circulated therethrough. In this manner, the module support member 12 can be placed at whatever operating temperature is desired for the chip 30. By reason of the thermal conduction between the module support member 12 and the chip 30 by way of the module 26, the chip 30 is also placed at the a temperature which is close to the temperature of the support member 12.

Referring again to FIGS. 2 and 3, the remainder of the positioner according to the present invention is illustrated standing on the plane 10. The mechanism of these two figures is designed to position a cooling device, indicated generally at 40, in a position where it is in contact with a chip 30. The various elements of the apparatus illustrated in FIGS. 2 and 3 will hereinafter be described in greater detail.

The positioning mechanism for positioning the cooling device 40 in contact with the chip 30 includes a plurality of legs 42 for supporting this mechanism above the base plane 10. The legs 42 couple at their upper end to a base member 44. The base member 44 is generally in a ring configuration thereby permitting it to encircle the module support member 12.

Movable member 46 rests on the base member 44 and is movable with respect thereto along a straight line. The direction of movement of the movable member 46 with respect to the base member 44 is said to be in the x direction. Movement of the movable member 46 with respect to the base member 44 is achieved by actuating a motor 48 which is attached to the base member 44 and has an actuator mechanism 50 which comes in contact with the movable member 46. The motor 48 causes the actuator 50 to move either left or right as illustrated in FIG. 2, thereby causing the movable member 46 which is coupled thereto to move either left or right as well. For reasons which will become clearer later, the position of the movable member 46 is sensed by an x position sensor 52. Accordingly, by actuating the motor 48 which preferably comprises a stepping motor, the position of the movable member 46 may be adjusted relative to the position of the module support member 12 as sensed by the x position sensor 52.

Disposed on the movable member 46 is a second base member 54. A second movable member 56 is rested upon the base member 54 in a manner permitting the movable member 56 to move in a direction which is orthogonal to the movement of the movable member 46 with respect to the base member 44. For convenience, the movable member 56 is said to be movable in the y direction which is defined as being orthogonal with respect to the x direction. Movement of the movable member 56 in the y direction is achieved by stepping the stepping motor 58 which causes the actuator 60 to move either left or right as illustrated in FIG. 3. The exact position of the movable member 56 is detected by a y position sensor 62.

The remaining portions of the positioner for disposing the cooling device 40 in contact with the chip 30 is mounted on the movable member 56 and extends upwardly therefrom.

As is best illustrated in FIG. 2, the remainder of the apparatus illustrated in FIG. 3 is pivotally attached to the movable member 56 and pivots or tilts about a tilt axis 70. The assembly above the movable member 56 can be manually tilted in the direction of the arrow 72 until the support legs 74 rest against the open position stop 76. In this position, it is possible for the operator to remove a cooling device 40 and replace it with a cooling device having a different design.

In normal operation of the tester according to the present invention, it is frequently desired to test a particular cooling device 40. It is of particular interest to be able to test the efficiency of a cooling device 40 when it does not mate properly with the chip 30 against which it is positioned by the mechanism of FIGS. 2 and 3. In this mode of operation, the tilt of the mechanism above the movable member 56 is controlled by a tilt stepping motor whose actuator 80 is movable in a direction indicated by the double headed arrow 81 and rests upon a stop 82. As illustrated in FIG. 2, a tilt position sensor is provided to measure the relative position of the mechanism attached to the movable member 56 for rotation about the axis 70.

Disposed on the upper end of the support legs 74 there is an intermediate support plate 86 on which the elements disposed above the plate 86 are supported. The plate 86 has a centrally disposed opening which has the member 88 projecting therethrough.

Disposed in parallel relation to the plate 86 is a second plate 90 which has a centrally disposed aperture for receiving a bushing member 92. The inner diameter of the bushing member 92 is sufficiently large so as to allow the movable member 88 to move up and down in a direction normal to the planar movement of the movable member 56.

Extending upwardly from the support plate 86 are a plurality of identical support legs 94. Positioned on the upper end of the support legs 94 is another support plate 96. Suspended from the support plate 96 are a plurality of support legs 98 which extend downwardly from the plate 96 and are connected to the support plate 90. As all the legs 98 are the same length and because the plate 96 is disposed parallel to the plate 86, the plate 90 is disposed parallel to the plate 86 as well.

Extending upwardly from the support plate 96 are a plurality of identical legs 100 whose uppermost end is secured to an upper support plate 102. Disposed on the upper support plate 102 is a downward force providing means 104 which may comprise a spring under compression or the like for producing a downwardly directed force against the z axis sense plane 106. The downward force producing means 104 therefore exerts a force along the z axis and against the z axis sense plane 106 which complements the forces of gravity to thereby push the sense plane in a direction toward the chip 30. Disposed on the upper support plate 102 is a z axis position sensor 108 which has a portion thereof projecting through the upper plate 102 and contacting the upper surface of the z axis sense plane 106. The z axis position sensor 108 provides suitable electrical signals for electrically sensing the position of the sense plane 106 with respect to the upper plate 102.

The sense plane 106 is mechanically coupled to the drive shaft of a rotational drive gear 110. The gear 110 is coupled to a smaller gear 112 which is disposed on the drive shaft of a stepping motor 114. By turning the drive shaft of the motor 114, the rotary position of the gear 110 can be established. In cooperation therewith, two limit defining pins 116 are mounted on the gear 110 and the position of these pins 116 is detected by a limit switch 118. As the gear 110 is generally movable in the vertical direction (z axis) relative to the plate 96, the motor 114 is mounted for movement in that direction as well so that it will move up and down as the gear 110 moves up and down.

The vertical position of the mechanisms mechanically coupled to the gear 110 is established by a ramp cam which is movable in a direction left and right as illustrated by the arrow 122. This movement is created by actuating a stepping motor 124 which is mechanically coupled thereto. The sloping surface of the ramp cam 120 is contained by a pair of spring loaded cam follower contacts 126 which are disposed on a cam follower carrier plate 128 which is mechanically coupled to the mechanism for supporting the motor 114 thereby permitting the carrier 128 to move in the z direction as the gear 110 does so as well. The ramp cam 120 is supported from below by a pair of rollers 130 which are rotatably mounted on the support plate 96. Accordingly, as the stepping motor 124 is actuated to move the ramp cam 120 either left or right, the linear movement of the cam 120 translates into vertical movement of all the members mechanically coupled to the cam follower carrier 128. As the vertically movable member 88 is coupled thereto as well, movement of the cam 120 in the direction indicated by the double headed arrow 122 results in vertical movement of the cooling device 40 which is coupled thereto.

As is best illustrated in FIG. 2, the vertically movable member 88 has a hollow passage 132 formed therein which couples between two external fittings 134 which, in operation of the apparatus of the present invention, is coupled by a suitable pipe to a liquid coolant source such as a container of water maintained at a selectable temperature. By passing such liquid through the passage 132, the temperature of the plug 136 which fits in the lowermost end of the body 88 and comes in contact with the liquid passing through the passage 132 can be controlled. As such, the temperature at the connection between the cooling device 40 and the plug 136 can be adjusted by controlling the temperature of the liquid passing through the passage 132.

In operation, the apparatus, as illustrated in FIG. 3, is surrounded by a bell jar 140 which rests upon the surface 110, and by means of a vacuum pump 142 or the like, the region disposed between the surface 10 and the bell jar 140 resting thereon can be placed in a vacuum. Alternatively, that region can be evacuated by the vacuum pump 142 and refilled with a gas having desired characteristics. The gas may comprise helium or air having a desired relative humidity. For most applications, however, it is believed that a vacuum would be most suitable for use of the apparatus according to the present invention as this will substantially eliminate radiation as a means for cooling the chip 30 thereby making possible accurate measurement of heat flow from the chip by means of a cooling device 40 when it is positioned in contact with chip 30.

Figure 6:
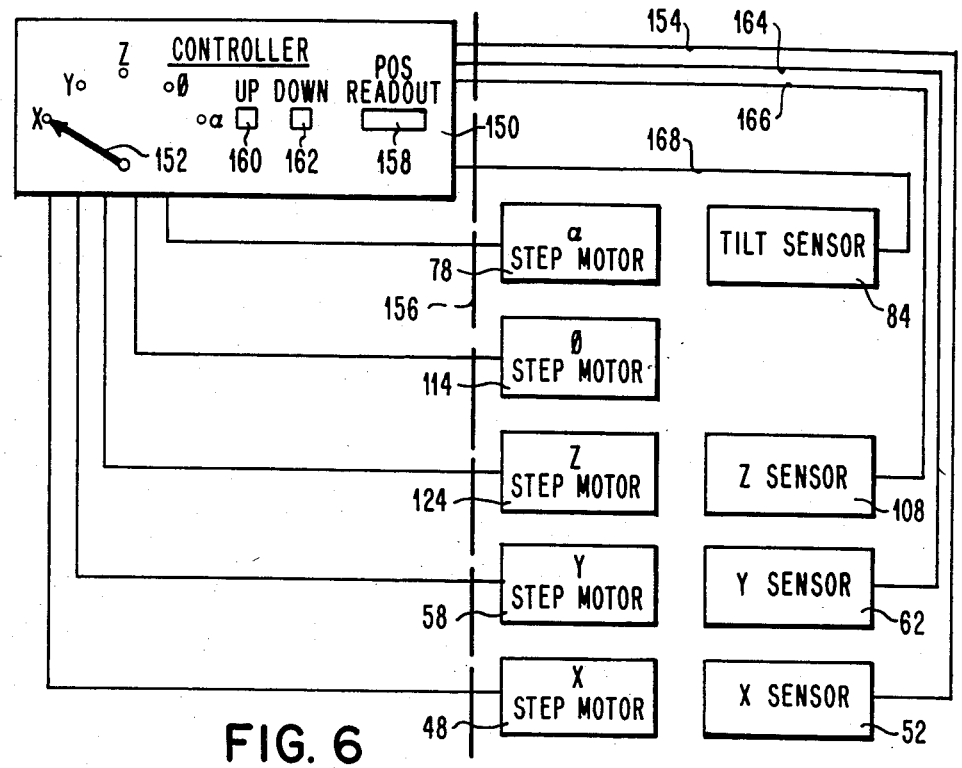
FIG. 6 is a block diagram of the control circuitry used to control the positioning mechanisms utilized in the invention.

Once the volume under the bell jar 140 has been evacuated by the vacuum pump 142, a test on the effectiveness on a cooling device 40 can be performed. In order to do so, however, the cooling device 40 must be positioned in contact with the chip 30. This contact may be established prior to evacuating the volume enclosed by the bell jar 140 and the surface 10 or may be accomplished after evacuation as desired. The positioning of the cooling device 40 is accomplished via the apparatus schematically shown in FIG. 6. That apparatus includes a controller 150 which has a selection knob or the like 152 which is manually positioned to the setting for adjusting one of the five adjustable elements of the apparatus as previously shown and described with reference to FIGS. 2 and 3. When the selector switch 152 is in "x" position as illustrated, the position of the movable member 46 in the x direction is sensed by the x position sensor 52 which is coupled by the wire 154 to the controller 150. It should be noted that the wire 154 passes through the base 110 (not illustrated in FIG. 2) in a manner which permits preserving the vacuum within the area enclosed by the bell jar 140. The passage through the base, however, is illustrated diagrammatically in FIGS. 6 by the fact that the line 154 passes through the dotted line 156 which is representative of the base 10 in FIGS. 2 and 3. Within the controller 150, the signal on the line 154 is converted into a position read out in a conventional manner and this read out is displayed on the position read out means 158. By pressing the up button 160 on the controller 150, the x stepping motor 48 is stepped in one direction thereby causing the movable member 46 to be displaced in that direction and the new position is sensed by the sensor 52 and subsequently displayed on the read out 158. Should movement in the opposite direction be desired, the operator merely has to depress the down button 162 which causes the stepping motor 48 to be stepped in the opposite direction thereby causing the member 46 to move in that direction. This causes the displayed position on the read out 158 to change to indicate the new x position.

In a similar fashion, the y, z and tilt sensors are coupled respectively by the lines 164, 166 and 168 to the controller 150. These controllable elements are controlled by the controller 150 in the same manner as has been already described with respect to x axis positioning. Control of the stepping motor 114, however, is performed in a slightly different manner. As there is no angle sensing means illustrated, although one could have been provided, the rotary motion is controlled in the following manner. The stepping motor 114 is advanced either by the up or down switch 160 or 162 respectively until one of the stop pins 116 engages the limit stop switch 118 which disengages the stepping motor 114. Thereafter, the stepping motor 114 is controlled by the other of the up/down buttons 160/162 to cause the motor 114 to turn in the opposite direction. The controller 150 counts the stepping pulses applied to the stepping motor and displays a number in the read out 158 corresponding to the number of degrees of rotation for each step. The value of rotation for each step can easily be determined by knowing the number of degrees that the rotor of the motor 114 turns per step and the gearing ratio between the engaged gears 112 and 110. In this manner, the rotation about the z axis can be precisely controlled.

Once the cooling device 40 is positioned as desired in thermal contact with the chip 30, the controller 150 is no longer required for the remainder of the test being performed with respect to the cooling device 40. The apparatus in FIG. 7, however, comes into active service at this time.

The chip utilized in the tester according to the present invention is preferably not a typical logic chip but comprises a specially fabricated chip for the purpose of testing cooling devices. The chip of the preferred embodiment includes a plurality of resistive elements located at various positions on the chip itself. These positions are selected in such a manner that if electrical power is applied to all of the resistors on the chip in a uniform fashion, the resulting temperature across the chip is not uniform due to the concentration of such resistive elements in some areas and the lack of resistive elements in other areas of the chip. This is done deliberately so as to more closely approximate the actual temperature distribution of digital electronic circuitry which might be placed on a chip and cooled by the cooling device under test.

The chip is also fabricated with a plurality of diodes positioned at various locations around the chip. These diodes are utilized to measure the temperature of the chip at the location of each of these diodes. As illustrated in FIG. 5, the substrate upon which the chip 30 is mounted has a plurality of pins such as pins 170 extending downwardly therefrom. These pins are connected in the normal fashion to the resistors and diodes disposed in the chip 30 located on the other side of the substrate as shown in FIG. 4. The pins 170, however, are coupled by a suitable electrical connection to a digital computer 172 as illustrated in FIG. 7, by a plurality of wires indicated by the arrows 174 and 176.

Figure 7:
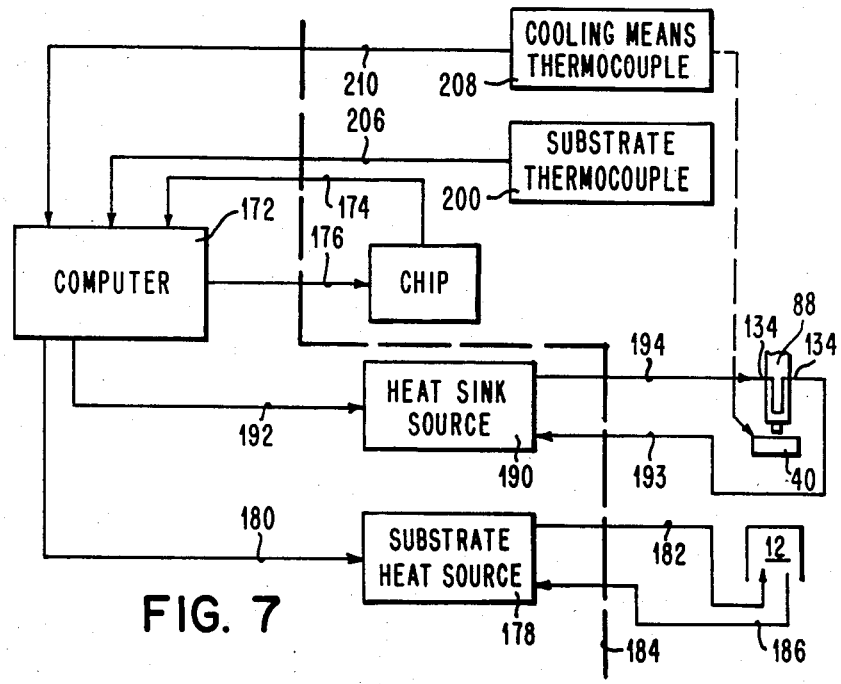
FIG. 7 is a block diagram of the temperature controlling apparatus of the invention which are used to assure that heat is carried away from the chip only by way of the cooling device.

The system, as illustrated in FIG. 7, includes a substrate heat source 178 which is utilized to heat the module support member 12 to a desired temperature. The substrate heat source typically comprises a reservoir for water or the like into which a heater has been placed. The heater receives control signals over the line 180 from the computer 172 for setting the temperature of the water in the reservoir to a desired temperature. In typical applications of the present invention, the temperature of the water is set to about 60° centigrade although temperatures higher or lower than that can be selected. The heated water is pumped by a suitable pumping mechanism via the pipes 182 through the base 10 as illustrated diagrammatically by the dotted line 184 to the module support member 12. The water passes through cavities within the module support member 12 and returns to the heat sense 178 via a pipe 186. By circulating water through the cavity within the module support member 12 at a temperature of approximately 60° centigrade, it is possible to thereby raise the temperature of the substrate attached thereto to a temperature approximately equal to the temperature of the liquid. The temperature selected for the substrate is approximately equal to the desired operating temperature of the chip itself during the test.

The system as illustrated in FIG. 7, also includes a heat sink source 190 which typically comprises a reservoir of water at a temperature selected by the computer 172 by sending signals over the line 192. In typical operation of the present invention, the liquid in the heat sink source 190 is at a temperature of approximately 25° C. although temperatures above or below that may be selected. The heat sink water is pumped by a suitable pumping means through the pipe 194 to the movable member 88. In this passage, the pipe 194 extends through the base wall as indicated by the dotted lines 184. The liquid also passes through the passage way 132 and exits via a pipe 196 to be returned to the heat sink source 190. In this fashion, a cooling source is provided to the cooling device 40.

The apparatus of FIG. 7 also includes a pair of thermocouples 200 which are mounted on the substrate on which the chip is mounted. The thermocouples 200 are provided for the purpose of monitoring the substrate temperature. As illustrated in FIG. 5, at 202 and 204, the thermocouples are disposed on the undersurface of the substrate at a position lying directly beneath the chip 30 and, therefore, serve as a means for measuring the substrate temperature at a point as closely as possible to that where the chip itself is mounted. The substrate thermocouples are connected by the leads 206 to the computer 172 and provide a means for providing the computer 172 with data representative of the substrate temperature.

A further thermocouple 208 is disposed on the cooling device 40 and this is coupled via the leads 210 to the computer 172. The thermocouple 208 provides the computer 172 with signals representative of the temperature of the cooling device 40 adjacent its coupling point with the movable member 88. As will be clear from FIG. 7, liquid is pumped from the heat sink source 190 through a pipe 194 to the coupling 134 on the movable member 88. The liquid passes through the member 88 and out through a second coupling 134 to a pipe 193 which returns the liquid to the heat sink source 190. It should be noted that the pipes 193, 194, 182 and 186 as well as the electrical leads 174, 176, 206 and 210, as illustrated in FIG. 7, pass through the dotted line 184 which is representative of the base plane 10 as shown in FIGS. 2 and 3. The pass through of these pipes and electrical wires is in a conventional manner which permits the atmosphere enclosed by the bell jar 140 to be precisely defined or for that to be a vacuum, as the case may be for the test in progress.

The computer 172 controls the apparatus of FIG. 7 in the following manner to perform a typical test on a cooling device 40. The computer 172 first specifies the temperature for the substrate and for the heat sink and signals representative thereof are transmitted over the lines 192 and 180, respectively to the heat sink source 190 and the substrate heat source 178. The temperature of the cooling liquid is then adjusted by the appropriate means within the sources 190 and 178 and these liquids are then pumped into the evacuated chamber so as to pre-establish the temperature for the upper surface of the cooling device 40 and for the substrate 26. Thereafter, electrical power is supplied to the chip over the lines 176 and the chip temperature is monitored over the lines 174. The computer 172 gradually raises the power into the chip until such time as the average temperature of the chip indicated by the signals received over the line 174 is equal to the temperature indicated by the substrate thermal couples 200 as sent over the line 206. When this condition is established in the steady state, the temperature of the chip and the temperature of the substrate are substantially equal and, accordingly, no heat flow occurs between the chip and the substrate. Accordingly, the heat generated within the chip itself must be flowing through the cooling device 40 to the heat sink provided by the fluid flowing through the movable member 88. The thermal resistance of the cooling device 40 can then be determined from the following equation: $(T_C - T_{CD}) / CP$ where $T_C$ is the chip temperature in degrees C, $T_{CD}$ is the temperature in degree centigrade of the cooling device and CP is the power in watts being provided to the chip by the computer 172. The smaller the measurement of thermal resistance corresponds to a cooling device of high efficiency.

It will be readily understood from the foregoing description that it will be possible to test a chip cooling device with the apparatus described above. By reason of the fact that the cooling device position is adjustable in five degrees of freedom relative to the chip being cooled by the apparatus illustrated, for example, in FIGS. 2 and 3, it is possible to test a cooling device at positions where optimal contact between the cooling device and the chip has not been established. The apparatus of the present invention can be useful, therefore, in determining the allowable cooling tolerance for a specific cooling device design. In addition, it will be possible to design alternative cooling devices having greater or lesser cooling efficiency that other designs. Such alternative designs may also be desirable as in certain applications, maximum cooling efficiency is undesirable as it may give rise to operating temperatures within a chip which are lower than would be desirable.

By reason of the fact that the cam followers 126 are spring loaded, vibration from the base can be transmitted to the member 88 and the cooling device 40 mounted thereon. As such, the thermal characteristics of the cooling device 40 can be tested in a manner which can identify the effect of vibration on cooling efficiency. This vibration test can be conducted when the cooling device is in a vacuum or the apparatus can be removed from the vacuum and vibrated and thereafter restored to the vacuum or controlled atmosphere for testing.

The design of the present invention also lends itself to easy temperature cycling of the chip and cooling device in situ. A clam shell arrangement is easily disposed around the cooling device and the chip. Heated or cooled gas can then be introduced into the area between the clam shells which enclose the chip and the cooling device. After performing the desired number of thermal cycles, the clam shells can be removed and the apparatus for supporting the chip and cooling device can then be returned to the controlled atmosphere inside the bell jar for additional measurement of the thermal resistance. In this way, the effect of thermal cycling on the cooling efficiency can be measured.

It should also be noted that the present apparatus is useful in measuring the thermal resistance of an interface between two bodies. It may also be used to measure the thermal resistance of a thermal paste. In this mode of operation, the cooling device 40 comprises the thermal paste or the interface itself. Calculation of the thermal resistance of a test conducted with such a physical arrangement will yield a thermal resistance for the interface between the chip and the tip of plug 136. Accordingly, the term "heat transfer device" as used in the following claims should be understood to include any heat transfer device such as a material used to form the interface between a heat producing body and a heat sink which includes a thermal paste, a gas, a metallurgical bond, or the like. The term also encompasses cooling devices as well. Indeed, the apparatus of the present invention measures all the thermal resistances between the chip which produces the heat in the first instance and the heat sink provided by the plug 136 of the illustrated embodiment.

The heat producing chip utilized in the present invention includes a plurality of heat producing regions resistor elements 252 which are not uniformly disposed in the chip. As such, the chip when powered does not have a uniform heat distribution therein. In addition, a plurality of heat sensing diodes are disposed at various positions as indicated by the dots 250 in FIG. 4 throughout the chip to measure the temperature at these various positions. The multiple temperature measuring diodes makes it possible to measure the thermal deviation on the chip itself as a means of further evaluating the performance of a particular cooling device.

From the foregoing description including various modifications to the preferred embodiment as illustrated in the drawings, it will be clear to those of skill in the art that numerous modifications may be made to the apparatus herein described without departing from the spirit and scope of the present invention as defined in the following claims.

What is claimed:

1. An apparatus for precisely measuring the thermal resistance of a heat transfer device for carrying heat away from a semiconductor chip comprising, in combination:

a heat source packaged in a housing having the size and configuration of a semiconductor chip to be cooled by a heat transfer device;

first temperature sensing means disposed on said heat source to sense the temperature of said heat source;

a support means for supporting said heat source in a thermal transfer relationship;

second temperature sensing means disposed to substantially measure the temperature of said heat source at the contact surface between said support means and said heat source;

positioning means in thermal contact with the heat transfer device at one end thereof for positioning the heat transfer device so that its other end is in thermal contact with said heat source so as to provide the desired heat transfer from said heat source to the heat transfer device;

third temperature sensing means disposed substantially at the contact between said positioning means and the heat transfer device;

means for placing the heat transfer device, said heat source, said first temperature sensing means, said support means, said second temperature sensing means, said positioning means and said third temperature sensing means in substantially a vacuum; and means to adjust the temperature of said support means, said heat source and said positioning means so that in the steady state heat generated by said heat source only flows through the heat transfer device toward said positioning means thereby making possible a determination of the thermal resistance of the heat transfer device.

2. The apparatus of claim 1 wherein said heat source includes a plurality of resistor elements disposed non-uniformly within said housing so as to heat said housing in a non-uniform manner.

3. The apparatus of claim 1 wherein first temperature sensing means includes a plurality of temperature sensors positioned at various points within said heat source to permit measuring the temperature of the heat source at a plurality of places therein thereby permitting the calculation of the average temperature within the heat source or temperature gradient across the heat source.

4. The apparatus of claim 1 wherein said support means includes a fluid passage for passing a fluid therethrough for causing the temperature of said support means to become substantially that of the fluid passing through said passage therethrough.

5. The apparatus of claim 4 wherein said means to adjust the temperature includes means for controlling the temperature of the fluid passing through said support means to thereby set the temperature thereof to be substantially that of the desired operating temperature of said heat source.

6. The apparatus of claim 1 wherein said positioning means includes a fluid passage for passing a fluid therethrough for causing the temperature of said positioning means substantially at the connection point with the heat transfer device to become that of the temperature of the fluid passing through said fluid passage therethrough.

7. The apparatus of claim 5 wherein said means to adjust the temperature includes means for controlling the temperature of the fluid passing through said positioning means to thereby set the temperature thereof to be substantially that desired.

8. The apparatus of claim 1 wherein said heat source includes a plurality of resistor elements disposed within said housing so as to heat said housing when electrical power is provided thereto.

9. The apparatus of claim 1 wherein said means to adjust the temperature includes heat source control means coupled to said heat source to control the electrical power applied thereto in response to the temperature measured by said first temperature sensing means, said heat source control means being operative to adjust the power to said heat source so that the temperature sensed by said first temperature sensor is substantially equal to the temperature sensed by said second temperature sensor.

10. The apparatus of claim 1 wherein said positioning means includes means to move said heat source relative to the heat transfer device in three degrees of freedom, two of said 3 degrees of freedom lying in a plane substantially parallel to the surface of said heat source surface in thermal contact with the heat transfer device and said third degree of freedom being substantially normal to said heat source surface in thermal contact with the heat transfer device.

11. An apparatus for measuring the thermal resistance of a heat transferring device comprising, in combination:

a heat source formed in the shape of a semiconductor chip and including a plurality of exterior surfaces, said heat source producing heat in response to electrical power being supplied thereto;

positioning means for supporting the heat transfer device for movement in at least five degrees of freedom relative to said heat source, said positioning means being operative to position the heat transfer device in thermal contact with at least one exterior surface of said heat source;

a base support for rigidly holding said heat source in a fixed position in thermal contact therewith;

vacuum means for enclosing said heat source, said positioning means and said base support in a vacuum;

means to cause the temperature of said base support to be substantially equal to the desired heat source operating temperature;

means to cause the temperature of said positioning means adjacent its connection to the heat transfer device to be equal to a desired temperature lower than said chip operating temperature; and means to adjust the temperature of said heat source so that the temperature thereof is substantially equal to the temperature of said base support thereby establishing the thermal resistance of the heat transfer device as $(T_C - T_{CD})/C_P$ where $T_C$ is the heat source temperature, $T_{CD}$ is the temperature of the positioning means adjacent the contact point with the heat transfer device and $C_P$ is the power supplied to said heat source.

12. The apparatus of claim 11 wherein said positioning means includes means to move the heat source carried thereby in two orthogonal degrees of freedom, lying in a plane, relative to said base support, said positioning means additionally including means to move said heat transfer device toward or away from said plane along a movement axis, means to tilt said movement axis relative to said plane and means to rotate the heat transfer device about said movement axis.

13. The apparatus of claim 12 wherein said positioning means permits vibrational movement of the heat transfer means along said movement axis.

14. The apparatus of claim 11 wherein said base support is made of a material having high thermal conductivity.

15. The apparatus of claim 14 wherein said base support is made of a material selected from the group consisting of copper or silver.

16. The apparatus of claim 11 wherein at least a portion of said positioning means is made of a high thermal conductivity material, said portion being disposed adjacent the connection point with the heat transfer device.

17. The apparatus of claim 16 wherein said high thermal conductivity material is selected from the group of silver or copper.

18. The apparatus of claim 11 wherein said heat source includes a plurality of resistor elements disposed non-uniformly therein.

19. The apparatus of claim 11 wherein a plurality of temperature sensing elements are disposed non-uniformly therein thereby making possible the calculation of either the average temperature thereof which comprises $T_C$ or the temperature differences between selected locations of said sensing elements disposed non-uniformly therein.

20. The apparatus of claim 11 wherein said base support has a passage therein for channeling a fluid therethrough for assuring that the temperature of said base support is that of a liquid which is passed therethrough.

21. a method for measuring the effect of thermal cycling on the operation of a chip cooling device comprising the steps of:
1. positioning a cooling device with respect to a chip, held by a chip holding means, in 5 degrees of freedom to a desired orientation of the cooling device with respect to the chip;
2. placing the cooling device, the chip, the chip holding means and the positioning means in a controllable atmosphere;
3. coupling a heat source to said chip holding means to raise the temperature of the chip holding means to the desired chip operating temperature;
4. applying power to the chip until its temperature is the same as said chip holding means thereby eliminating heat flow from the chip through said chip holding means;
5. determining the thermal resistance of the cooling device from the equation $(T_C - T_D)/P$ where $T_C$ is the measured chip temperature, $T_D$ is the measured temperature of the of the cooling device and P is the power applied to the chip;
6. removing the chip, the chip holding means, the positioning means and cooling device from said controllable atmosphere and thermal cycling the chip and the cooling device in situ; and
7. repeating steps 2–5.

22. The method of claim 21 additionally including the step of placing the cooling device and chip under vibration after step 5 and before step 7 to thereby vibrationally degrade the contact between the cooling device and the chip.

23. A method for measuring the effect of vibration on the operation of a chip cooling device comprising the steps of:
1. positioning a cooling device with respect to a chip, held by a chip holding means, in 5 degrees of freedom to a desired orientation of the cooling device with respect to the chip;
2. placing the cooling device, the chip, the chip holding means and the positioning means in a controllable atmosphere;
3. coupling a heat source to said chip holding means to raise the temperature of the chip holding means to the desired chip operating temperature;
4. applying power to the chip until its temperature is the same as said chip holding means thereby eliminating heat flow from the chip through said chip holding means;
5. determining the thermal resistance of the cooling device from the equation $(T_C - T_D)/P$ where $T_C$ is the measured chip temperature, $T_D$ is the measured temperature of the of the cooling device and P is the power applied to the chip;
6. vibrating the cooling device relative to the chip; and
7. repeating steps 3–5.

24. A method for measuring the thermal resistance of a chip cooling device comprising the steps of:
1. positioning a cooling device with respect to a chip, held by a chip holding means, in 5 degrees of freedom to a desired orientation of the cooling device with respect to the chip;
2. placing the cooling device, the chip, the chip holding means and the positioning means in a controllable atmosphere;
3. coupling a heat source to said chip holding means to raise the temperature of the chip holding means to the desired chip operating temperature;
4. applying power to the chip until its temperature is the same as said chip holding means thereby eliminating heat flow from the chip through said chip holding means; and
5. determining the thermal resistance of the cooling device from the equation $(T_C - T_D)/P$ where $T_C$ is the measured chip temperature, $T_D$ is the measured temperature of the of the cooling device and P is the power applied to the chip.

* * * * *